United States Patent [19]

Florek

[11] Patent Number: 4,589,406
[45] Date of Patent: * May 20, 1986

[54] ORTHOPAEDIC APPLIANCE FOR USE IN TREATING ACROMIOCLAVICULAR JOINT INJURIES

[76] Inventor: Florian F. Florek, 104 High St., Edinboro, Pa. 16412

[*] Notice: The portion of the term of this patent subsequent to Nov. 6, 2001 has been disclaimed.

[21] Appl. No.: 521,990

[22] Filed: Aug. 11, 1983

[51] Int. Cl.$^4$ ............................................. A61F 5/04
[52] U.S. Cl. .................................. 128/87 R; 128/94; 128/DIG. 19
[58] Field of Search ............... 128/87 R, DIG. 19, 94, 128/133; 604/362

[56] References Cited

U.S. PATENT DOCUMENTS

| | | | |
|---|---|---|---|
| 3,141,456 | 7/1964 | Meek | 128/DIG. 19 |
| 3,338,236 | 8/1967 | McLeod, Jr. | 128/87 |
| 3,718,137 | 2/1973 | Gaylord, Jr. | 128/87 R |
| 3,856,004 | 12/1974 | Cox | 128/DIG. 19 |
| 3,857,388 | 12/1974 | Frankel | 128/87 R |
| 3,906,944 | 9/1975 | Christen | 128/DIG. 19 |
| 3,965,907 | 6/1976 | Hardy et al. | 604/362 |
| 4,188,944 | 2/1980 | Augustyniak | 128/94 |

OTHER PUBLICATIONS

McLeod Padded Clavical Splint Instruction Sheet (May, 1978).
Zimmer Patient Care Systems, p. PC21.
Howmedica, Inc., Orthopaedics Division Brochure, p. G-14.
Fractures and Other Injuries, Chapter 17, pp. 254-258, 1958-1961.

Primary Examiner—John D. Yasko
Attorney, Agent, or Firm—Howson and Howson

[57] ABSTRACT

A splint designed specifically to treat acromioclavicular joint sprains and dislocations is disclosed. The splint includes a connector pad adapted to be placed against the patient's back below the base of the neck and a pair of clavicle straps which diverge from the connector pad and extend over both clavicles and under both axillae and which are adjustably connected to the connector pad. A pressure pad is interposed between one of the straps and the distal end of the clavicle. The pressure pad cooperates with an auxiliary strap extending along the patient's back for connecting the upper and lower runs of the clavicle strap and thereby aiding in the application of pressure in desired directions to the clavicle and acromion to promote healing. Each clavicle strap has a tubular pad which contains an elongated radio-opaque marker strip useful in treating the patient.

18 Claims, 5 Drawing Figures

ORTHOPAEDIC APPLIANCE FOR USE IN TREATING ACROMIOCLAVICULAR JOINT INJURIES

FIELD OF THE INVENTION

The present invention relates to medical devices, and more particularly, the present invention relates to splints designed specifically for treating sprains and/or separations of the acromioclavicular joint.

BACKGROUND OF THE INVENTION

A common type of shoulder injury often seen by the practicing physician involves a sprain or separation of the acromioclavicular joint. The acromioclavicular joint, or A-C joint as it is sometimes called, connects the distal end of the clavicle with the underlying acromion which overlies the upper end of the humerus, or upper arm. A sprain or separation is generally caused by a downward blow to the shoulder.

There are various grades of injury to the A-C joint, ranging from sprains to separations, or dislocations. A sprain is defined as an injury to a joint with possible rupture of ligaments but without dislocation. A dislocation, or separation, is defined as an injury to a joint involving rupture of the ligaments and dislocation of the joint. There are various grades of sprains and dislocations ranging from grade I (mild) through grade II (moderate) to grade III (severe).

Depending upon the severity of the injury, surgery may be required to effect proper reparation of the joint. Surgery has the disadvantages of leaving external scars which can be objectionable, especially to female patients. Moreover, with surgery, there are the risks of possible infection, not to mention the need for hospitalization, general anesthesia, and the discomfort associated with the surgical procedure. This is particularly true where a complete separation has occurred thereby requiring the use of a pin and the removal of the pin in a subsequent operation after restoration has been effected.

BRIEF DESCRIPTION OF THE PRIOR ART

Various devices have been proposed for non-surgically restoring acromioclavicular joints. One such device includes a strap which extends over the affected shoulder and under the opposite arm in somewhat of a diagonal manner across the patient's chest. An arm sling receives the patient's elbow and has a pair of straps which extend upwardly along the anterior and posterior portions of the patient's chest to connect to the strap. A disadvantage of this type of device is that it immobilizes the patient's arm, thereby adversely interfering with the patient's normal day to day activities.

U.S. Pat. No. 4,188,944 discloses another type of acromioclavicular restoration brace. It includes a vertically disposed oval primary strap which holds a pressure pad over the acromioclavicular joint while simultaneously applying upward pressure to the joint via the humerus and acromion. A secondary strap encircles the upper portion of the patient's chest to hold the pad in position above the acromioclavicular joint. The secondary strap may also be used to immobilize the patient's arm. With this device, downward pressure is applied to both the distal end of the clavicle and the acromioclavicular joint, while upward pressure is being applied via the humerus.

For many years it has been customary to treat fractured clavicles using the so-called figure-of-eight splint. Such a splint includes a common pad normally placed against the patient's back and from which a pair of padded straps diverge and extend over the clavicles and under the axillae before returning to the pad and being connected thereto. Such a splint is intended to press downward on the distal end of the clavicle while raising the acromion. Figure-of-eight splints have not been generally used in treating acromioclavicular joint sprains and/or separations.

OBJECTS OF THE INVENTION

With the foregoing in mind, a primary object of the present invention is to provide a novel splint which is particularly suited for use in treating acromioclavicular joint sprains and/or separations in a non-surgical manner.

Another object of the present invention is to provide an improved splint which overcomes the limitations of known prior art splints, or braces, used to restore acromioclavicular joint separations.

A further object of the present invention is to provide a unique splint which is designed to restore acromioclavicular joint separations with a minimum of inconvenience to the patient.

A still further object of the present invention is to provide an acromioclavicular joint restoration splint designed to apply forces in desirable directions and magnitudes to promote restoration of the acromioclavicular joint with a minimum of discomfort to the patient. Yet another object of the present invention is to provide an acromioclavicular joint restoration splint and method of using the same to treat a wide variety of degrees of injury to the acromioclavicular joint without the need for surgery.

SUMMARY OF THE INVENTION

More specifically, the present invention provides an improved acromioclavicular restoration splint which is designed to treat sprains and/or separations of the acromioclavicular joint with a minimum of patient discomfort and inconvenience. The splint comprises a connector pad which is adapted to be placed against the patient's back below the base of the neck and a pair of padded clavicle straps diverging from the connector pad and extending over both clavicles and under both axillae with free ends releasably fastened to the connector pad. Pressure pad means is applied over the distal end of the clavicle and is engaged by one of the clavicle straps for causing pressure to be applied downwardly to the distal end of the clavicle while pressure is being applied upwardly via the portion of the padded clavicle strap extending through the axilla. An auxiliary strap connects the upper run of the clavicle strap and depends downwardly therefrom in a generally vertical direction to connect with the lower run of the clavicle strap between the connector pad and the axilla. The upper end of the auxiliary strap has a loop which slidably receives the clavicle strap and which cooperates with hook and pile type releasable fastening means to prevent slippage when the auxiliary strap is tightened. Preferably, each of the clavicle straps has an elongated tubular pad which contains a strip of radio-opaque barium sulfate marker material which is useful in treating the patient. The auxiliary strap cooperates with the clavicle strap and the pressure pad to apply pressure in the desired direction and amount to promote restoration and healing of the acromioclavicular joint.

BRIEF DESCRIPTION OF THE DRAWINGS

The foregoing and other objects, features and advantages of the present invention should become apparent from the following description when taken in conjunction with the accompanying drawings, in which.

DESCRIPTION OF THE PREFERRED EMBODIMENT

Figure 1:
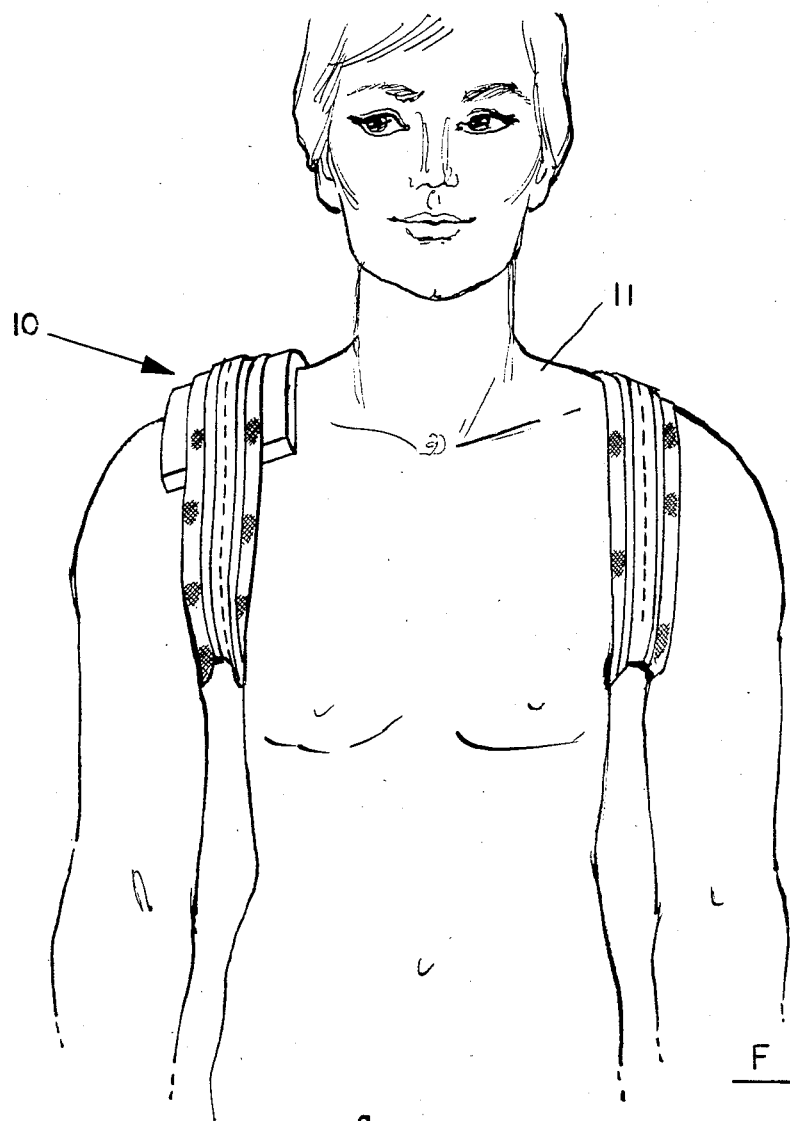
FIG. 1 is an anterior view of an adult male shown wearing the acromioclavicular restoration splint which embodies the present invention.

Referring now to the drawings, FIG. 1 illustrates a splint 10 which embodies the present invention and which is shown applied to an adult male patient 11. The patient 11 is shown being treated with the splint 10 for an injury to the right acromioclavicular joint. It is to be understood, of course, that the splint of the present invention may be used to treat injuries of either or both shoulders of either male or female patients of various stature and age.

Before discussing in detail the manner in which the splint 10 of the present invention functions to heal acromioclavicular joint injuries, a brief review of certain of the more important anatomical features of the patient's bones and ligaments is believed to be in order.

Figure 3:
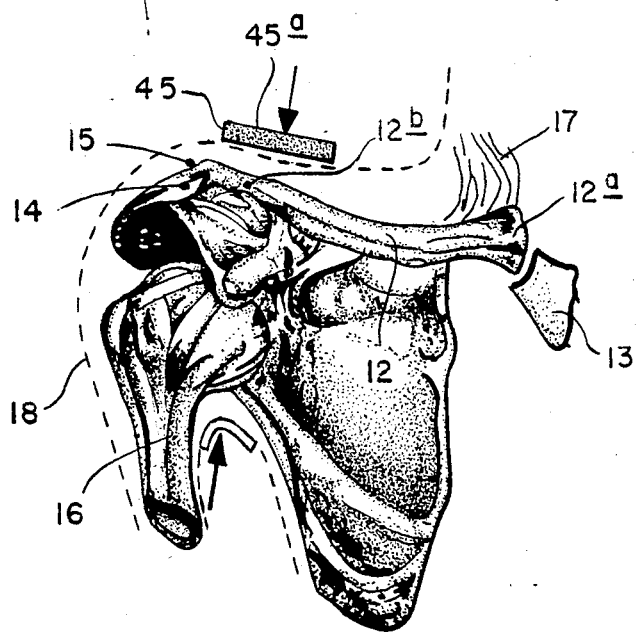
FIG. 3 is an anterior view of certain of the bones and ligaments forming the patient's shoulder, the view illustrating schematically certain elements of the splint of the present invention in a relation to certain features of the anatomy.

Referring now to FIG. 3, which is a view of the patient's right shoulder, the clavicle 12 is the slightly curved bone which extends in a generally horizontal direction between the sternum 13 on the right and the acromion 14 on the left. The proximal end 12a of the clavicle 12 is joined to the sternum 16, and its distal end 12b is joined to the acromion 14 by means of the acromioclavicular joint 15. The acromion 14 overlies the upper end of the humerus, or upper arm, 16. The clavicular portion of the sternocleidomastoid muscle 17 extends upwardly from the proximal end 12a of the clavicle 12 in the neck of the patient 11. The skin which covers the aforementioned anatomical structure is indicated by the broken line 18.

Most sprains and/or separations of the acromioclavicular joint 15 occur as a result of a downward blow to the acromion 14. This causes the acromion 14 to pull away from the distal end 12b of the clavicle 12 stretching, and in some cases, tearing the connecting tissue and ligaments. Depending upon the severity of the blow, the distal end 12b of the clavicle 12 can even be separated completely from the acromion 14.

The present invention provides a splint 10 which is designed to restore the distal end 12b of the clavicle 12 to its proper juxtaposition with respect to the acromion 14 for promoting healing of the ligaments and tissues of the acromioclavicular joint 15. According to the present invention, the aforementioned restoration and healing is the result of the direct application of pressure in the downward direction to the distal end 12b of the clavicle 12 and in an upward direction to the acromion 14. As a result, pressure is applied in a desired amount and direction directly to the affected joint, as contrasted with prior art splints, or braces, wherein the pressure to the acromion is applied to the joint 15 via the humerus 16.

Figure 4:
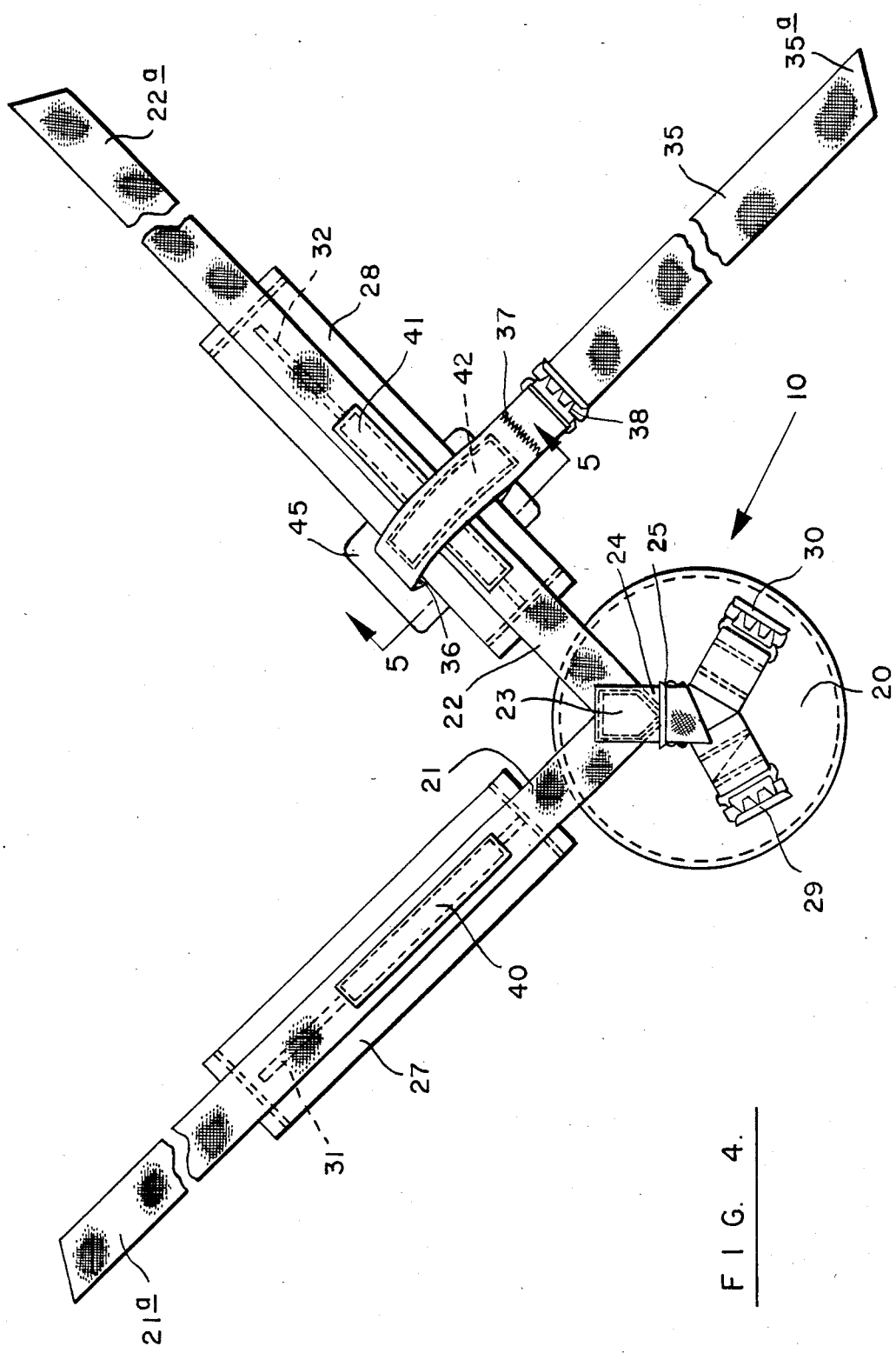
FIG. 4 is a plan view illustrating the splint of the present invention layed out prior to application to the patient.

As best seen in FIG. 4, the splint 10 comprises a padded circular connector pad 20 adapted to be placed against the patient's back below the base of the neck in the manner illustrated in FIG. 2. A pair of elongated clavicle straps 21 and 22 are connected together at a common location 23 and diverge therefrom in a generally V-shaped configuration. A short tab 24 is connected at the juncture 23 of the straps 21 and 22 and is connected via a buckle 25 to the connector pad 20 to afford limited vertical adjustment of the connector pad 20 relative to the patient's anatomy. Preferably, the tab 24 is relatively short so that the juncture 23 of the straps 21 and 22 is maintained within the upper outer periphery of the connector pad 20, and preferably as close as possible to the center of the circular pad 20. This arrangement has been found to be effective in preventing the connector pad 20 from riding up along the patient's back. The straps 21 and 22 are fabricated of low stretch webbing, such as the webbing used in conventional figure-of-eight splints.

In order to distribute pressure applied by the straps 21 and 22, elongated tubular pads 27 and 28 of knitted stockinette fabric are sewn at their opposite ends to the straps 21 and 22, such as the pad 27 sewn to the left hand strap 21 and a like pad 28 similarly sewn to the right hand strap 22. The elongated pads 27 and 28 are shorter in length than the lengths of the straps 21 and 22, thereby leaving the straps 21 and 22 with free end portions 21a and 22a which are adapted to be connected in the buckles 29 and 30 carried by the connector pad 20 at angles in the manner illustrated. The pads 27 and 28 are of a length sufficient as to pass over both of the patient's clavicles and under his axillae such as in the manner illustrated in FIG. 2. The buckles 29 and 30 function in a conventional manner to afford adjustment of the length of the straps 21 and 22 and hence adjustment of the pressure applied thereby. Preferably, the elongated pads 27 and 28 each have a length of about 18 inches, a width of about 3 inches, and a thickness of about ½ inch, and each is connected about 3 inches from the common juncture 23. The pads 27 and 28 are preferably knitted of cotton fiber of relatively low density to provide softness, flexibility and washability.

For purposes to be described, the elongated pads 27 and 28 have sewn within each a strip of radio-opaque marker material, such as the lengths 31 and 32 illustrated in dotted lines inside the pads 27 and 28, respectively in FIG. 4. Preferably, the radio-opaque marker strips 31 and 32 are formed of barium sulfate and run the entire length of the pads 27 and 28. The marker strips 31 and 32 are preferably held in position inside their tubular pads 27 and 28 by zigzag stitching (not shown) running lengthwise of the pads 27 and 28. Preferred barium sulfate strips have a diameter of at least about two millimeters and are sold under the trade designation RAY-TEC. Strips of such size have been found to provide a readily visible image on an X-ray print as will be discussed.

In order to ensure the application of pressure to the affected joint in the proper direction and in the desired amount, the splint 10 has an auxiliary strap 35 which can be connected to either of the clavicle straps 31 and 32 depending, of course, on which of the patient's acromioclavicular joints has been injured and is to be treated. In the embodiment of FIG. 4, the auxiliary strap 35 is shown connected to the right hand clavicle strap 22 corresponding with an injury to the patient's right shoulder, such as illustrated in FIGS. 1 and 2. As best seen in FIG. 4, the upper end of the auxiliary strap 35 is reversely turned to form a loop 36 which is sewn onto itself by stitching 37. The loop 36 is sufficiently large as to slidably receive the clavicle strap 22 and pad 28 which is secured thereto. A buckle 38 is fastened to the auxiliary strap 35 adjacent the stitching 37, and it functions to receive the free end 35a of the strap 35 to enable its length, and hence tension, to be adjusted.

The position of the auxiliary strap 35 is adjustable lengthwise of the padded clavicle strap 22 and is also adjustable angularly with respect thereto. For this purpose, a pair of pile fabric strips 40 and 41 are sewn on the upper surface of the straps 21 and 22, respectively over the zone of the pads 27 and 28. The strips 40 and 41 are disposed toward the inner ends of the pads 27 and 28, i.e. adjacent the connector pad 20 so as to overlie the clavicles when on the patient. See FIG. 2.

In order to secure the loop 36 of the auxiliary strap 35 in any adjusted position, a strip of hooks 42 is sewn on the inside of the strap 35 and is disposed to overlie the pile strips, such as the pile strip 41. The strip of hooks 42 cooperates with the strip of pile fabric 41 in a well known manner to prevent relative sliding motion between the auxiliary strap 35 and the clavicle strap 22 after the adjustment has been made and the straps pressed together. The disposition of the pile fabric strips 40 and 41 on both of the clavicle straps 21 and 22 enables the auxiliary strap 35 to be used with either the left or right clavicle strap 21 or 22, depending upon the location of the acromioclavicular joint separation to be treated. The strip of hooks 42 and pile fabric strips 40 and 41 are of well-known Velcro construction.

Figure 5:
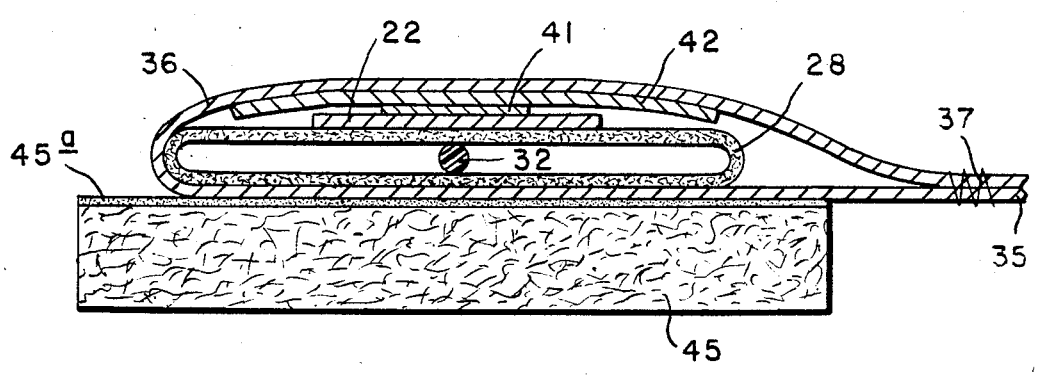
FIG. 5 is an enlarged, fragmentary sectional view taken on line 5—5 of FIG. 4.

For the purpose of applying pressure to the distal end of the clavicle it is important for at least one or more fiber pressure pads, such as the pad 45, to be provided underneath the clavicle pad 28. The pressure pad 45 preferably comprises a rectangular block of felt fibrous material which is interposed between the tubular clavicle pad 28 and the patient's skin. The fiber pad 45 may be sewn to the underside of the loop 36 of the auxiliary strap 35, such as illustrated in FIG. 5, or it may be fastened to the elongated pressure pad 28. Preferably, however, the pressure pad 45 has a pressure sensitive adhesive layer 45a which releasably adheres to the auxiliary strap 35 such as in the manner shown in FIG. 5. This allows the auxiliary strap loop 36 to be slid relative to the padded strap 22 into various adjusted positions. If desired, the pressure pad 45 may be adhered directly to the patient's skin over the affected clavicle.

Figure 2:
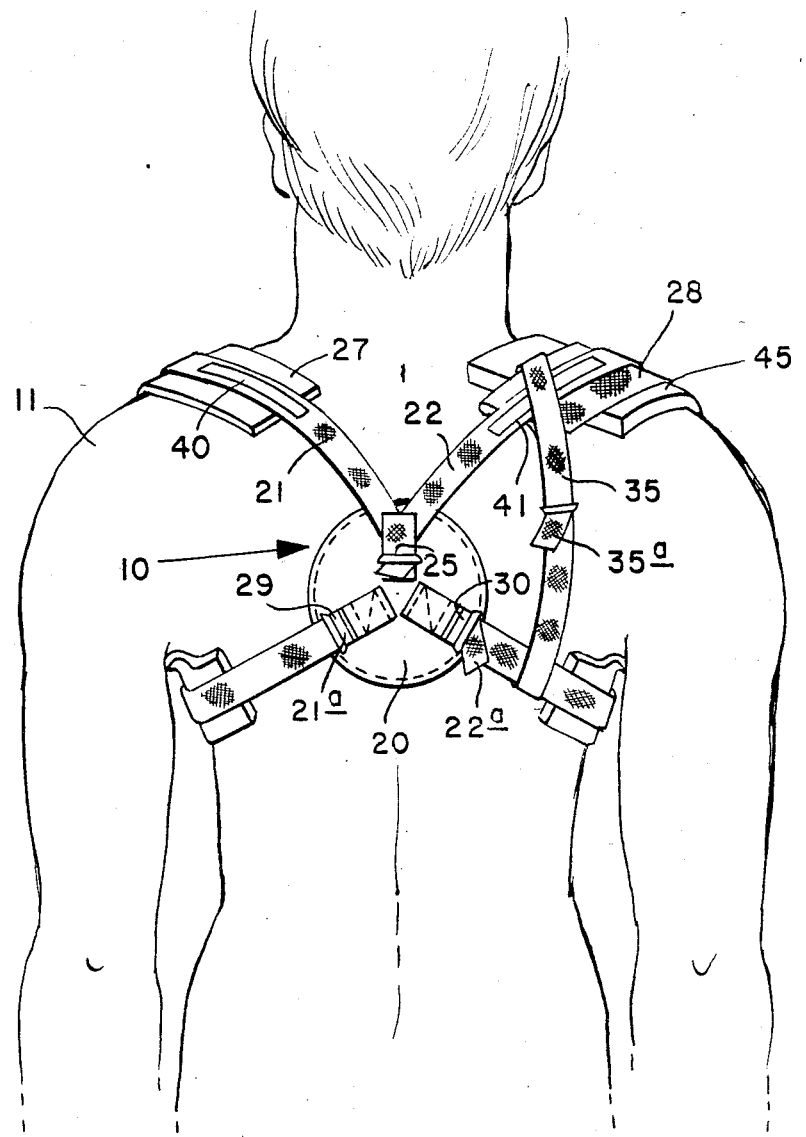
FIG. 2 is a posterior view of the patient wearing the splint.

When the splint 10 is applied to the patient 11 in the manner illustrated in FIGS. 1 and 2, the right hand padded clavicle strap 22 engages the pressure pad 45 and applies pressure downwardly over the distal end 12b of the clavicle 12 in the direction indicated by the arrow in FIG. 3. Simultaneously, upward pressure is applied to the acromion 14 via the return run of the clavicle strap 22 which passes under the right axilla and which applies pressure in the direction indicated by the arrow in FIG. 3. These opposing pressures cooperate to press the distal end 12b of the clavicle 12 against the acromion 14 and to maintain the same in such relation for the purpose of promoting healing of the acromioclavicular joint 15. The period of application of the pressure will, of course, depend on the severity of the injury and the judgment of the treating physician as determined by periodic examination and X-rays of the affected area. If desired, a conventional arm sling may also be used to apply upward pressure to the acromion and to immobilize the arm should such steps be indicated by the nature and severity of the injury.

To ensure the application of pressure in the desired amount and direction, the auxiliary strap 35 is placed by the treating physician in the position indicated in FIG. 2, i.e. running substantially vertically across the back of the patient 11 and extending between the upper run of the right padded clavicle strap 22 and the return portion thereof between the connector pad 20 and the injured acromioclavicular joint. Normally, the physician adjusts the location of the loop 36 of the auxiliary strap 35 with respect to the padded clavicle strap 22 by sliding the same therealong and pressing the hook and pile fasteners together before passing the strap 35 under the lower run of the clavicle strap 22 and through the buckle 38 and then pulling on the free end 35a of the auxiliary strap 35 to tighten it. In this manner, the auxiliary strap 35 can be tensioned to assist in relieving pressure at the base of the patient's neck and in applying pressure to the distal end 12b of the clavicle 12 via the felt pad 45 since it forms something like a noose around the affected joint. The pressure can also be adjusted by pulling the free ends 21a and 22a of the clavicle straps 21 and 22 through their respective buckles 29 and 30 connected to the connector pad 20. If additional pressure is desired, it can be readily applied simply by superimposing additional pads on top of the pressure pad 45. This has the effect of increasing pressure in the desired location without requiring excessive amounts of tension in the clavicle straps. Thus, when installed in the manner illustrated in FIGS. 1 and 2, the auxiliary strap 35 cooperates with the right hand clavicle strap 22 and the pressure pad 45 to apply pressure in the desired direction and amount to press the distal end of the clavicle 12b against the acromion to promote healing the same.

To assist the physician in adjusting the splint 10 to ensure application of pressure in the desired location, and to assist him in explaining to the patient the biomechanics involved in the treatment, X-ray photographs are taken of the affected shoulder after the splint has been applied. The X-rays reveal the location of the radio-opaque marker strip 32 which is carried by the padded clavicle strap 22 as it passes around the injured acromioclavicular joint 15. Since the marker strip 32 is carried in the center of the clavicle strap, it aids the physician in pinpointing the zone of pressure application by the splint 10 and enables him to make appropriate adjustments in the clavicle strap 22 and auxiliary strap 35 to ensure the application of pressure in the proper amount and direction. The image of the marker strip 32 on the X-ray also enables the physician to explain to the patient the biomechanics involved in the application of pressure and the need for wearing the splint 10 in a particular manner.

In view of the foregoing, it should be apparent that a new method has been developed for utilizing an improved figure-of-eight type splint to promote healing of acromioclavicular joint sprains and/or separations. The method includes the steps of placing at least one pad over the distal end of the clavicle, engaging the upper run of a clavicle strap against the pad to ensure the application of pressure in a downward direction to the distal end of the clavicle, while simultaneously engaging the return run of the clavicle strap with the patient's axilla to cause pressure to be applied upwardly to the acromion. Preferably, the upper and lower runs of the clavicle strap are pulled together, or tensioned between the patient's spinal column and the acromioclavicular joint undergoing treatment with an auxiliary strap to form something like a noose around the affected joint. With this method, the distal end of the clavicle and the acromion are brought together in proper juxtaposition for healing with the direct application of pressure to the affected area. This is to be contrasted with the conventional splints or braces used to treat acromioclavicular joint dislocations which normally require the application of upward pressure via the humerus.

While a preferred orthopaedic appliance and method of treatment have been described in detail, various modifications, alterations and changes may be made without departing from the spirit and scope of the present invention as defined in the appended claims.

I claim:

1. For use in treating a patient having an acromioclavicular joint injury wherein the distal end of the patient's clavicle is out of its normal position with respect to the underlying acromion, a splint comprising:
    a connector pad adapted to be placed against the patient's spinal column below the base of the neck,
    a pair of clavicle straps diverging from said connector pad and having upper portions adapted to extend forwardly over both clavicles and having lower portions extending under both axillae and returning to said connector pad,
    means adjustably connecting said lower portions of said straps to said connector pad,
    means providing a pressure pad overlying the distal end of the injured clavicle and engaging one of said clavicle straps,
    an auxiliary strap disposed along the patient's back between the spinal column and the distal end of the injured clavicle, said auxiliary strap being connected at its upper end to said one clavicle strap adjacent said pressure pad means and being connected at its lower end to the lower portion of said one clavicle strap,
    said one clavicle strap cooperating with said auxiliary strap and said pressure pad means to apply pressure in a downward direction to the distal end of the injured clavicle and in an upward and inward direction to the acromion for urging the same together,
    whereby the splint applies pressure in a desirable direction to the acromioclavicular joint to promote healing of the same.

2. The splint according to claim 1 wherein said auxiliary strap has a loop at its upper end slidably receiving said one clavicle strap, and including cooperating hook and pile fastening means on said one clavicle strap and said loop for releasably securing said auxiliary strap to said one clavicle strap in adjusted positions.

3. The splint according to claim 2 wherein said hook and pile fastening means includes complementary strips of hooks and pile, one of said strips being disposed on the inside of said loop and the other of said strips extending lengthwise on at least said one clavicle strap.

4. The splint according to claim 3 wherein said one strip is composed of said hooks and said other strip is sewn onto both of said clavicle straps.

5. The splint according to claim 1 wherein said auxiliary strap has means for engaging a reversely turned portion thereof and releasably fastening the same to afford lengthwise adjustment of said auxiliary strap between said upper and lower portions of said one clavicle strap.

6. The splint according to claim 1 wherein said pressure pad means has a surface adapted to engage the patient's skin over the clavicle, and including means on said pressure pad for adhesively securing said pressure pad means in place over the clavicle.

7. The splint according to claim 6 wherein said pressure pad is disposed with said adhesive means engaging one of said clavicle straps.

8. The splint according to claim 1 including an elongated radio-opaque marker strip disposed lengthwise along at least a portion of the length of at least said one clavicle strap.

9. The splint according to claim 8 including elongated tubular pads carried by said clavicle straps, and wherein said radio-opaque marker material includes a length of barium sulfate secured inside each of said tubular pads.

10. The splint according to claim 1 including a tab connected to said clavicle straps where they join together and buckle means carried by said connector pad for releasably securing said tab at selected adjusted vertical positions within the periphery of said connector pad.

11. For use in treating acromioclavicular joint injuries, a splint comprising:
    a connector pad,
    a pair of elongated clavicle straps connected at a common location to said pressure pad and diverging therefrom in a generally V-shaped manner,
    a pair of elongated pads extending lengthwise of said straps for a portion of their lengths,
    an auxiliary strap having a loop for slidably receiving one of said clavicle straps,
    complementary means on said pair of clavicle straps and said auxiliary strap loop for releasably fastening said auxiliary strap to a selected one of said clavicle straps at selected adjusted positions,
    means on said connector pad for releasably securing said clavicle straps thereto while affording lengthwise adjustment thereof relative to said connector pad, and
    means on said auxiliary strap to afford tensioning thereof between upper and lower portions of said one clavicle strap when applied to a patient.

12. The splint according to claim 11 wherein said tensioning means on said auxiliary strap includes a buckle for receiving the free end of said auxiliary strap and releasably securing the same to itself to afford said tensioning of said auxiliary strap.

13. The splint according to claim 11 including a fiber block pad carried by said auxiliary strap loop and releasably connected thereto by a pressure sensitive adhesive layer on said fiber block.

14. The splint according to claim 11 including a strip of radio-opaque marker material extending lengthwise in each of said elongated pads.

15. The splint according to claim 11 wherein said complementary fastening means includes a strip of pile fabric secured to each clavicle strap in the zone of the elongated pad, and a strip of hooks secured to the inside of said auxiliary strap loop and adapted to releasably engage said pile fabric strip for securing said auxiliary strap to said clavicle strap.

16. For use in treating a patient having an acromioclavicular joint injury wherein the distal end of the patient's clavicle is out of its normal position with respect to the underlying acromion, a splint comprising:
   a connector pad adapted to be placed against the patient's spinal column below the base of the neck,
   a pair of clavicle straps diverging from said connector pad and having upper portions adapted to extend forwardly over both clavicles and having lower portions extending under both axillae and returning to said connector pad,
   means adjustably connecting said lower portions of said straps to said connector pad, and
   an elongated strip of radio-opaque marker material carried lengthwise by each of said clavicle straps, whereby the strips of marker material assist in observing the zones of pressure application by the splint.

17. A method of treating a patient having an injured acromioclavicular joint, comprising the steps of:
   disposing at least one pad over the distal end of the patient's clavicle,
   engaging against said pad the upper run of a clavicle strap to apply downward pressure to the distal end of said clavicle,
   engaging under the patient's axilla the lower run of the clavicle strap to apply upward and inward pressure to the patient's acromion,
   tensioning said upper and lower runs of said clavical strap, and
   pulling said upper and lower runs of said clavicle strap toward one another along the patient's back adjacent to the acromioclavicular joint undergoing treatment to form a noose for applying directly to the acromioclavicular joint a desired amount of pressure in said upward and downward directions during healing.

18. A splint comprising:
   a connector pad adapted to be placed against a patient's spinal column below the base of the neck,
   a pair of clavicle straps diverging from said connector pad and having upper portions adapted to extend forwardly over both clavicles and having lower portions extending under both axillae and returning to said connector pad,
   means adjustably connecting said lower portions of said straps to said connector pad, and
   an elongated strip of radio-opaque marker material carried lengthwise by at least one of said clavicle straps,
   whereby the strip of marker material enables a treating practitioner to use X-ray procedures for observing zones of pressure applied by the splint.

* * * * *